United States Patent [19]
Conkerton

[11] 3,948,733
[45] Apr. 6, 1976

[54] SIMPLIFIED PROTEIN HYDROLYSIS APPARATUS

[75] Inventor: Edith J. Conkerton, New Orleans, La.

[73] Assignee: The United States of America as represented by the Secretary of Agriculture, Washington, D.C.

[22] Filed: Dec. 12, 1973

[21] Appl. No.: 423,959

[52] U.S. Cl. ................................. 195/142; 23/259
[51] Int. Cl.² .......................................... C12B 1/14
[58] Field of Search ........... 195/126, 127, 139, 142; 23/230 B, 253 R, 292, 259, 290; 215/307, 311; 251/148, 309; 128/218 N

[56] References Cited
UNITED STATES PATENTS 2,706,702    4/1955    Carski................................ 195/126

Primary Examiner—A. Louis Monacell
Assistant Examiner—R. B. Penland
Attorney, Agent, or Firm—M. Howard Silverstein; Max D. Hensley

[57] ABSTRACT

This invention relates to a new simplified apparatus to hydrolyze proteins either in vacuo or under an atmosphere of nitrogen. More specifically, this invention consists of a sample mixture chamber attached in a seal tight manner to an inert fitting means with a tapered outlet which is connected to a two-way valve with a tapered inlet. The valve has a sealed on-off control device, and a lock connector attached to the outlet to allow an evacuating device to be connected.

3 Claims, 1 Drawing Figure

U.S. Patent   April 6, 1976   3,948,733
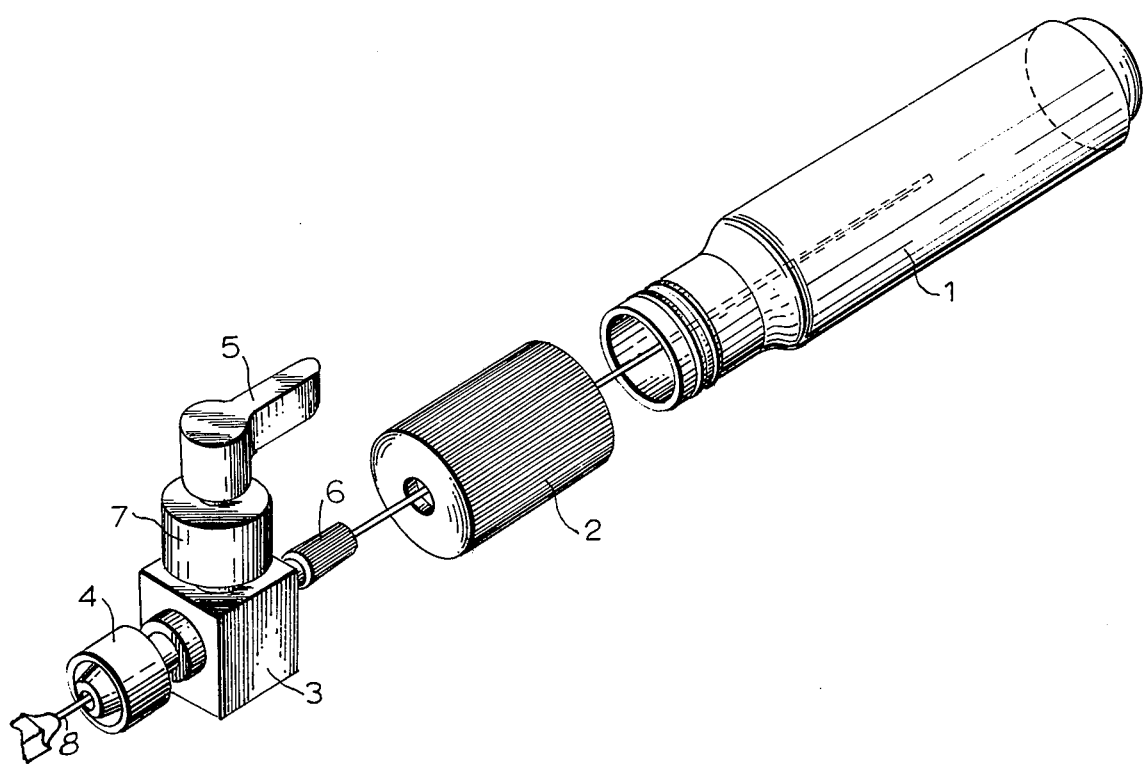

NEW SIMPLIFIED PROTEIN HYDROLYSIS APPARATUS

PRIOR ART

Traditionally, proteins have been hydrolyzed in a sealed glass ampoule either in vacuo or under an atmosphere of nitrogen. Because a high temperature flame and considerable dexterity is required to seal the ampoule, several modifications of the apparatus have been attempted. Most of these, however, conduct the hydrolysis either in vacuo or in an atmosphere of nitrogen. Recently, Darbre (Lab. Practice 20, 720, 1971) reported a system in which hydrolysis can be accomplished under either condition. However, his apparatus requires the services of a glassblower for the modification of special stopcocks and appears to be limited to micro or semi-micro samples. Since the apparatus is glass it is unwieldly and fragile.

OBJECTIVES

The apparatus described here can be used in vacuo or under nitrogen, does not require special glassblowing modifications, can accommodate sample weights normally used in analysis of crude or purified proteins, yields reproducible results, eliminates unwieldliness and fragility of apparatus, allows versatility of sample size, and costs a minimal amount to fabricate.

GENERAL DESCRIPTION OF INVENTION

This is a simplified apparatus devised to hydrolyze proteins consisting of the following: A hole is drilled in the top of a teflon-lined screw cap to allow the tapered inlet connection, e.g., a Luer taper, of an on-off control, e.g., a two-way Hamilton Valve, to be pushed into the cap and extend just below the lining to form a gas-tight seal. The hole thus serves as an inert fitting means for the tapered inlet connection. The outlet of the Hamilton Valve has a Luer Lok connector attachment 4 which serves as a means to connect the on-off control to an evacuating device. The screw cap is capable of being affixed to a chamber, e.g., a culture tube, for retaining the sample to be assayed. A sample is weighed into the culture tube and the appropriate amount of 6 N HCl is added. A strip of teflon tape is wrapped around the threads on the neck of the tube and the screw cap fitted with the valve is tightened in place. If the sample is to be evacuated, the tube and its contents are frozen in a dry ice-acetone bath and vacuum applied by attaching the Luer lock connector of the unit to a vacuum pump before opening the valve. The procedure outlined by Moore and Stein, (Methods in Enzymology 6, 819, 1963), can then be followed. If an atmosphere of nitrogen is desired, the gas is introduced via a capillary inserted through the opened valve. After the atmosphere within the tube has been purged, the capillary is withdrawn and the valve closed. Adjustment of the packing nut around the on-off valve control provides a positive seal.

DETAILED DESCRIPTION OF INVENTION

The invention will be described by reference to the single FIG. 1 of drawing, showing an exploded view of the device, and an illustrative experiment which was performed for the purpose of describing the preferred embodiment of the invention.

As illustrated in FIG. 1, a hole is bored in the top of the Teflon-lined screw cap 2 to allow the Luer taper 6 of the Hamilton valve 3 to be pushed into the cap, extending just below the lining to form a gas-tight seal. The sample is weighed into the culture tube 1 and the appropriate amount of 6N HCl added. A strip of Teflon tape is wrapped around the threads on the neck of the tube and the screw cap fitted with the valve is tightened in place. If the sample is to be evacuated, the tube and contents are frozen in a dry ice-acetone bath and vacuum applied by connecting the unit to a vacuum pump before opening the valve lever 5. The procedure as outlined by Moore and Stein (Methods in Enzymology 6, 819, 1963) can then be followed.

If an atmosphere of nitrogen is desired, the gas is introduced via a capillary 8 inserted through the opened valve 3. After the atmosphere within the tube has been purged, the capillary is withdrawn and the valve closed. Adjustment of the packing nut 7 provides a positive seal.

Samples have been successfully hydrolyzed at 110° centigrade ± 1°C (about 16 pounds per square inch pressure) for 20 hours in a forced air oven or in an aluminum block heater and at 145°±2°C (about 59 pounds per square inch pressure) for 4 hours in the aluminum block heater.

In these studies, 3–5 mg samples of purified proteins and 10–30 mg samples of solvent extracted oilseed meals were hydrolyzed, respectively, in culture tubes of 8 and 15 ml capacity. However, by use of tapered reaction vials of 0.3 ml capacity or screw-cap centrifuge bottles of 200 ml capacity, the sample size could range from 0.5 mg to 900 mg.

After hydrolysis, the sample is cooled to room temperature before the modified cap is replaced by a regular cap. HCl can be removed on a rotary evaporator or under a stream of nitrogen at 100°C in the block heater. If amino acid analysis is to be carried out by gas chromatography, derivatization can be accomplished in the same tube thereby avoiding possible error due to an additional transfer step; if by ion exchange, the sample can be suspended in buffer and a suitable aliquot removed for application to the column.

A recent study of precision in amino acid analysis by Kwolek and Cavins (J.A.O.A.C. 54, 1283, 1971) concluded that relative standard deviations (RSD) of amino acid values for independently hydrolyzed samples should be no greater than 25%. Comparison of literature values for bovine serum albumin (Tristram, G. R., and Smith, R. H., Advan. Protein Chem. 18, 276, 1963) to data obtained on a sample of this protein hydrolyzed by the technique described here showed RSD's of 25% for lysine and threonine, 14% for glycine, 11% for isoleucine and 9% or less for all others. Data from a solvent extracted peanut meal analyzed at this laboratory after hydrolysis in vacuo according to Kurtzman et al. (Anal. Biochem. 12, 282, 1965) compared with data from the same material hydrolyzed under the conditions described here showed RSD's of 20% for serine, 17% for isoleucine, 14% for valine, 13% for threonine, 12% for leucine, 10% for lysine, and 7% or less for all others.

The initial cost of the entire unit is minimal and it can be fabricated without special tools. The valves and tubes can be used indefinitely while caps, which should be used only once, can be easily replaced.

I claim:

1. A new simplified hydrolyzing apparatus capable of operating under a positive pressure, comprising:
   a. a chamber for placing a sample mixture,
   b. an inert fitting means for attaching the chamber to a tapered connection,
   c. a two-way valve containing an on-off control with a leak-proof sealing means, and a Luer taper inlet connection capable of attaching to said inert fitting means,
   d. a means to connect the two-way valve to an evacuating device, said hydrolyzing apparatus capable of retaining positive internal pressures from about 16 to about 59 pounds per square inch.

2. The apparatus of claim 1 wherein the chamber is a culture tube.

3. The apparatus of claim 1 wherein the inert fitting means for attaching the chamber to the taper connection is a teflon-lined screw cap open on one end to fit the culture tube and on the other to fit the Luer taper.

* * * * *